(12) United States Patent
Nord et al.

(10) Patent No.: US 11,684,800 B2
(45) Date of Patent: Jun. 27, 2023

(54) APPARATUS TO FACILITATE THE ADMINISTRATION OF A KNOWLEDGE-BASED RADIATION TREATMENT PLAN

(71) Applicants: Varian Medical Systems International AG, Steinhausen (CH); Varian Medical Systems, Inc., Palo Alto, CA (US)

(72) Inventors: Janne I. Nord, Espoo (FI); Joona Hartman, Espoo (FI); Esa Kuusela, Espoo (FI); Corey Zankowski, San Jose, CA (US)

(73) Assignees: Varian Medical Systems International AG, Steinhausen (CH); Varian Medical Systems, Inc., Palo Alto, CA (US)

( * ) Notice: Subject to any disclaimer, the term of this patent is extended or adjusted under 35 U.S.C. 154(b) by 343 days.

(21) Appl. No.: 16/926,990

(22) Filed: Jul. 13, 2020

(65) Prior Publication Data

US 2020/0338362 A1    Oct. 29, 2020

Related U.S. Application Data

(63) Continuation of application No. 15/662,799, filed on Jul. 28, 2017, now Pat. No. 10,744,342.

(51) Int. Cl.
*A61N 5/10* (2006.01)
*G16H 50/50* (2018.01)

(52) U.S. Cl.
CPC .......... *A61N 5/103* (2013.01); *A61N 5/1031* (2013.01); *G16H 50/50* (2018.01)

(58) Field of Classification Search
CPC ............... A61N 5/103; A61N 5/1038; A61N 2005/1041; A61N 5/1031; G16H 50/50
USPC ............................................. 600/1
See application file for complete search history.

(56) References Cited

U.S. PATENT DOCUMENTS

| 10,744,342 B2 * | 8/2020 | Nord ............... G16H 50/50 |
| 2012/0136194 A1 * | 5/2012 | Zhang ............. A61N 5/103 600/1 |
| 2015/0094519 A1 | 4/2015 | Kuusela et al. |
| 2017/0177812 A1 | 6/2017 | Sjölund |

OTHER PUBLICATIONS

Extended European Search Report from European Patent Application No. 18184632.0 dated Nov. 28, 2018; 6 pages.

* cited by examiner

*Primary Examiner* — Sunita Reddy
(74) *Attorney, Agent, or Firm* — Fitch, Even, Tabin & Flannery LLP

(57) ABSTRACT

A control circuit accesses information regarding a plurality of pre-existing vetted radiation treatment plans for a variety of patients and uses that information to train at least one model (such as a dose volume histogram estimation model). The control circuit then uses that model to develop estimates for a radiation treatment plan for a particular patient. The control circuit can then use those estimates to develop a candidate radiation treatment plan.

18 Claims, 5 Drawing Sheets

APPARATUS TO FACILITATE THE ADMINISTRATION OF A KNOWLEDGE-BASED RADIATION TREATMENT PLAN

CROSS-REFERENCE TO RELATED APPLICATION

This is a continuation of U.S. patent application Ser. No. 15/662,799, filed Jul. 28, 2017, now U.S. Pat. No. 10,744, 342, which is hereby incorporated herein by reference in its entirety.

TECHNICAL FIELD

These teachings relate generally to the use of radiation as a therapeutic treatment and more specifically to the formation and use of corresponding radiation-treatment plans.

BACKGROUND

The use of radiation to treat medical conditions comprises a known area of prior art endeavor. For example, radiation therapy comprises an important component of many treatment plans for reducing or eliminating unwanted tumors. Unfortunately, applied radiation does not inherently discriminate between unwanted areas and adjacent healthy tissues, organs, or the like that are desired or even critical to continued survival of the patient. As a result, radiation is ordinarily applied in a carefully administered manner to at least attempt to restrict the radiation to a given target volume.

Treatment plans typically serve to specify any number of operating parameters as pertain to the administration of such treatment with respect to a given patient. Such treatment plans are often optimized prior to use. (As used herein, "optimization" will be understood to refer to improving upon a candidate treatment plan without necessarily ensuring that the optimized result is, in fact, the singular best solution.) Many optimization approaches use an automated incremental methodology where various optimization results are calculated and tested in turn using a variety of automatically-modified (i.e., "incremented") treatment plan optimization parameters.

Treatment plan optimization techniques, such as so-called inverse planning, typically requires the setting of optimization objectives. Generally speaking, setting optimization objectives has traditionally relied upon experienced users. Such persons have often learned, through practice, that "easy" objective can lead to a sub-optimal plan while "hard" objective can lead to sub-optimal trade-offs. And even experienced users often find themselves tethered to an iterative process that is frequently demanding of repeated interaction in these regards.

BRIEF DESCRIPTION OF THE DRAWINGS

The above needs are at least partially met through provision of the apparatus to facilitate the administration of a knowledge-based radiation treatment plan described in the following detailed description, particularly when studied in conjunction with the drawings, wherein.

Figure 1:
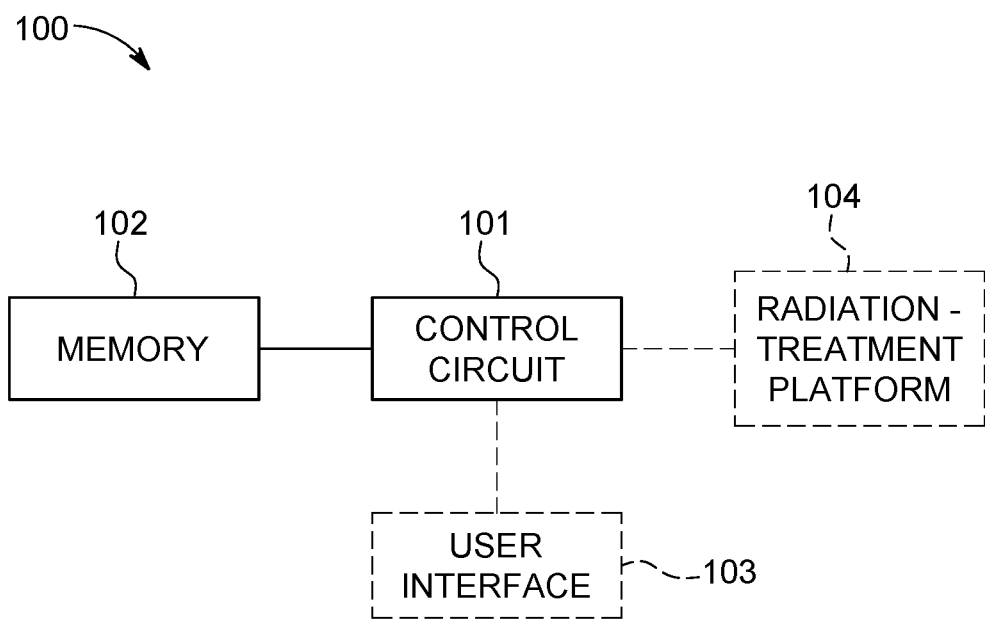
FIG. 1 comprises a block diagram as configured in accordance with various embodiments of these teachings.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present teachings. Also, common but well-understood elements that are useful or necessary in a commercially feasible embodiment are often not depicted in order to facilitate a less obstructed view of these various embodiments of the present teachings. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein.

DETAILED DESCRIPTION

Generally speaking, pursuant to these various embodiments a control circuit accesses information regarding a plurality of pre-existing vetted radiation treatment plans for a variety of patients and uses that information to train at least one model. The control circuit then uses that model to develop estimates for a radiation treatment plan for a particular patient. The control circuit can then use those estimates to develop a candidate radiation treatment plan.

By one approach, the aforementioned information regarding the plurality of pre-existing vetted radiation treatment plans for a variety of patients constitutes an abridged version of such plans such that the information is anonymous and not intrinsically correlated to any of the patients. In a typical application setting the source pre-existing vetted radiation treatment plans may have differing original formats from one to the next. In such a case, if desired, these teachings will accommodate presenting the aforementioned information to the control circuit using a single consistent format.

By one approach the control circuit uses the aforementioned information to train a model by, at least in part, identifying outlier data in the information and avoiding relying upon such outlier data when training the model. By another approach, in lieu of the foregoing or in combination therewith, when training the model the control circuit can use original prescription dose levels as correspond to at least some of the pre-existing vetted radiation treatment plans (for example, by using the original prescription dose levels when normalizing dose volume histograms).

When using the aforementioned model to develop estimates for a radiation treatment plan for a particular patient, by one approach the control circuit uses metadata corresponding to the source information to select suitable content with which to train the model.

By one approach the control circuit uses geometric limits corresponding to the aforementioned information to assess how well a particular patient fits the information used to train the model. When the particular patient does not fit the information used to train the model within at least a predetermined range of suitability, these teachings will accommodate presenting a corresponding warning to the user.

These teachings will also accommodate having the control circuit determine at least one radiation treatment plan objective for use when optimizing a resultant radiation treatment plan for a particular patient by forming one or more radiation treatment plan objectives based upon dose volume histogram estimates that the control circuit formed using the aforementioned model. If desired, these teachings will accommodate providing a user opportunity to permit the user to modify one or more such automatically determined radiation treatment plan objectives.

These teachings are highly flexible in practice and will accommodate a wide variety of modifications and additional activity. As one example in these regards, the control circuit can be configured to determine a validation status of the aforementioned model and inhibit availability of that model when the validation status has other than a predetermined value/level. This inhibited availability may comprise, for example, preventing publication of the corresponding model to a wider audience.

So configured, these teachings provide a system that can be used, for example, to collect a set of pre-existing and previously-utilized treatment plans and to generate one or more dose estimation models at least partially (or fully) based thereon. This system can further estimate DVH's based on such a model and facilitate generating objectives based on those DVH's. This system can also facilitate sharing the estimation and objective model with other users including users of other institutions/clinics. In all of the foregoing sharing opportunities the source information derived from actual patients can be highly anonymized to protect patient privacy while also reducing any corresponding computational processing loading.

These and other benefits may become clearer upon making a thorough review and study of the following detailed description. For the sake of an illustrative example it will be presumed for the purpose of the following description that a control circuit of choice carries out some or all of the described activities. FIG. 1 presents one example of an enabling apparatus 100 in these regards.

In this particular example, the enabling apparatus 100 includes such a control circuit 101. Being a "circuit," the control circuit 101 therefore comprises structure that includes at least one (and typically many) electrically-conductive paths (such as paths comprised of a conductive metal such as copper or silver) that convey electricity in an ordered manner, which path(s) will also typically include corresponding electrical components (both passive (such as resistors and capacitors) and active (such as any of a variety of semiconductor-based devices) as appropriate) to permit the circuit to effect the control aspect of these teachings.

Such a control circuit 101 can comprise a fixed-purpose hard-wired hardware platform (including but not limited to an application-specific integrated circuit (ASIC) (which is an integrated circuit that is customized by design for a particular use, rather than intended for general-purpose use), a field-programmable gate array (FPGA), and the like) or can comprise a partially or wholly-programmable hardware platform (including but not limited to microcontrollers, microprocessors, and the like). These architectural options for such structures are well known and understood in the art and require no further description here. This control circuit 101 is configured (for example, by using corresponding programming as will be well understood by those skilled in the art) to carry out one or more of the steps, actions, and/or functions described herein.

The control circuit 101 operably couples to a memory 102. This memory 102 may be integral to the control circuit 101 or can be physically discrete (in whole or in part) from the control circuit 101 as desired. This memory 102 can also be local with respect to the control circuit 101 (where, for example, both share a common circuit board, chassis, power supply, and/or housing) or can be partially or wholly remote with respect to the control circuit 101 (where, for example, the memory 102 is physically located in another facility, metropolitan area, or even country as compared to the control circuit 101).

In addition to information regarding a plurality of pre-existing vetted radiation treatment plans for a variety of patients as described herein, this memory 102 can serve, for example, to non-transitorily store the computer instructions that, when executed by the control circuit 101, cause the control circuit 101 to behave as described herein. (As used herein, this reference to "non-transitorily" will be understood to refer to a non-ephemeral state for the stored contents (and hence excludes when the stored contents merely constitute signals or waves) rather than volatility of the storage media itself and hence includes both non-volatile memory (such as read-only memory (ROM) as well as volatile memory (such as an erasable programmable read-only memory (EPROM).)

The control circuit 101 may also optionally include a network interface. So configured the control circuit 101 can communicate with other elements (both within the apparatus 100 and external thereto) via such a network interface. Network interfaces, including both wireless and non-wireless platforms, are well understood in the art and require no particular elaboration here.

By one optional approach the control circuit 101 operably couples to a user interface 103. This user interface 103 can comprise any of a variety of user-input mechanisms (such as, but not limited to, keyboards and keypads, cursor-control devices, touch-sensitive displays, speech-recognition interfaces, gesture-recognition interfaces, and so forth) and/or user-output mechanisms (such as, but not limited to, visual displays, audio transducers, printers, and so forth) to facilitate receiving information and/or instructions from a user and/or providing information to a user.

Figure 2:
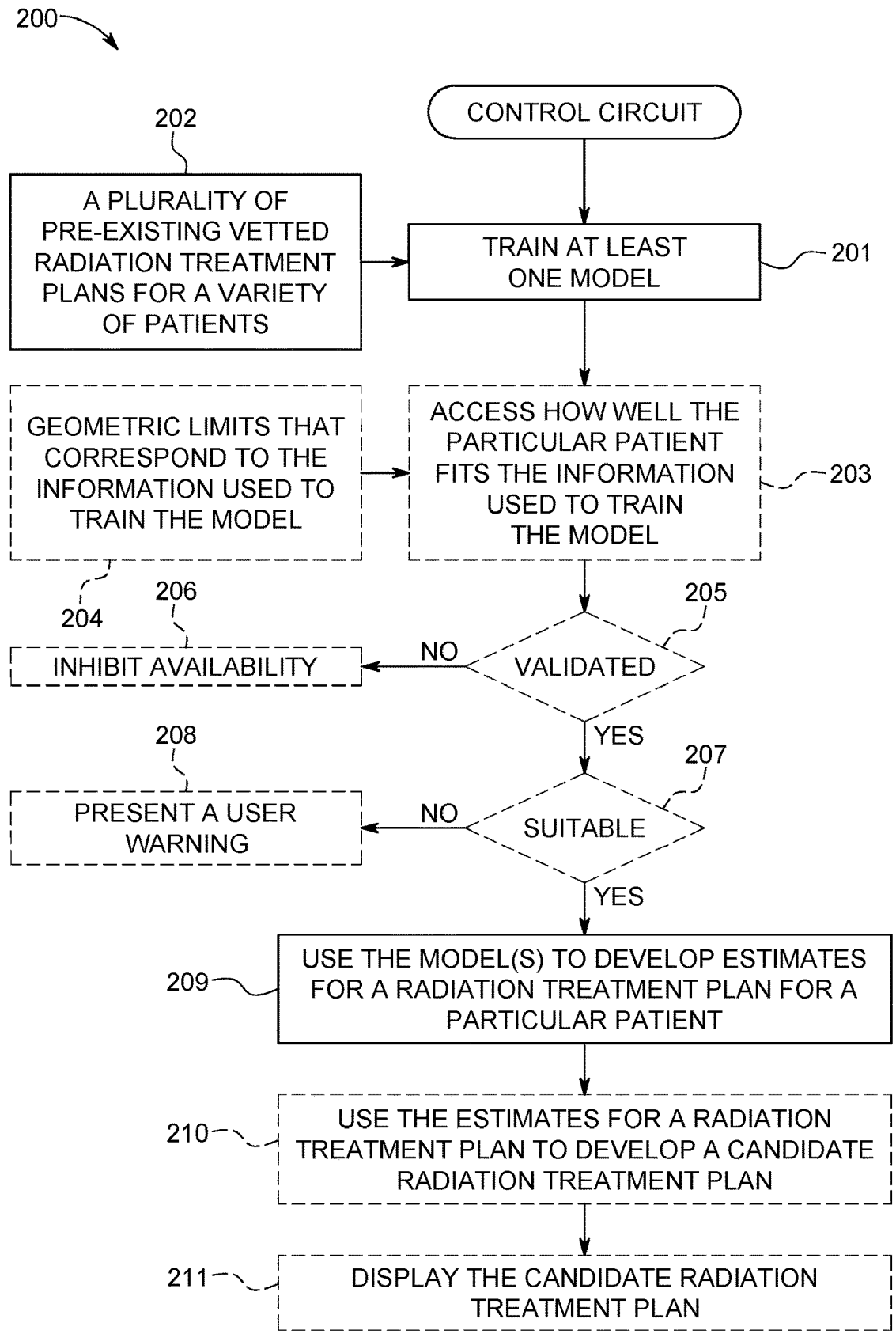
FIG. 2 comprises a flow diagram as configured in accordance with various embodiments of these teachings.

FIG. 2 presents a process 200 that can be carried out, in whole or in part, by the aforementioned control circuit 101. At block 201 the control circuit 101 uses information to train at least one model. In this example the information comprises information 202 regarding a plurality of pre-existing vetted radiation treatment plans for a variety of patients. This information can be accessed, for example, by retrieving the information from the aforementioned memory 102. As used herein, the word "vetted" means that these radiation treatment plans were not only previously devised and optimized, but have also been approved by a relevant final authority for use and/or has actually been utilized to administer a radiation treatment to the corresponding patient. Accordingly, these plans do not represent mere academic or virtual exercises but are plans that have seen real-world clinical usage.

Generally speaking, these teachings anticipate extracting useful information from those pre-existing vetted radiation treatment plans prior to and separately from the model training activities described herein.

By one approach this process 200 will accommodate using pre-existing vetted radiation treatment plans having original formats that are different from one another. In particular, the information 202 accessed by the control circuit 101 regarding these plans can comprise content where the information regarding these pre-existing vetted radiation treatment plans has a single consistent format.

By one approach, and for the sake of an illustrative example to be used herein, the model comprises a dose volume histogram (DVH) estimation model.

DVH's typical represent three-dimensional dose distributions in a graphical two-dimensional format (the three-dimensional dose distributions being created, for example, in a computerized radiation-treatment planning system based on a three-dimensional reconstruction of an X-ray computed tomography scan and study). The "volume" referred to in DVH analysis can be, for example, the radiation-treatment target, a healthy organ located near such a target, an arbitrary structure, and so forth.

DVH's are often visualized in either of two ways: as differential DVH's or as cumulative DVH's. With differential DVH's column height for a given dose bin corresponds to the volume of the structure that receives that dose. Bin doses typically extend along the horizontal axis while structure volumes (either percent or absolute volumes) extend along the vertical axis.

A cumulative DVH is typically plotted with bin doses along the horizontal axis but has a column height for the first bin that represents the volume of structure(s) that receive greater than or equal to that dose. The column height of the second bin then represents the volume of structure(s) that receive greater than or equal to that dose, and so forth. With high granularity a cumulative DVH often appears as a smooth line graph. For many application settings cumulative DVH's are preferred over differential DVH's but this process 200 can accommodate either approach.

In this example the information used to train a DVH estimation model can include various parameters from exemplary patient cases. Examples of such parameters include parameters calculated from planned dose distribution matrices and parameters representing complex geometric relationships in corresponding patients. As noted, these pre-existing vetted radiation treatment plans are for a corresponding variety of patients.

That said, this information 202 (such as the aforementioned parameters) can comprise an abridged version of the corresponding radiation treatment plans. For example, by one approach the information comprises, at least to a large extent, only the aforementioned extracted parameters. Specific examples of such information can include biological structure sets or descriptions, dose prescriptions, and field geometry information but not any information that can specifically identify a particular patient such as names, images that present the person's face, or the like. The information is therefore anonymous and is not outwardly intrinsically identifying of any of the patients. Accordingly, the privacy of these patients is preserved. If desired, such anonymity makes it considerably easier to share such information from one enterprise/institution to another.

It will also be appreciated that extracting these relevant parameters prior to providing the information to the control circuit 101 results in a considerably smaller data set than the original data set. This can speed up the pre-training data acquisition process and can also result in faster training of the model, hence potentially avoiding any need for a technologically upgraded or faster control circuit 101.

By one approach more than one DVH estimation model may be trained for a particular treatment situation (each model typically being specific to a certain use rather than to only a certain patient). For example, a separate model may be utilized for each organ at risk as well as the target volume. These teachings will also accommodate partitioning organs at risk into qualitatively different sub-volumes that may each have different DVH estimation requirements.

The foregoing can be appropriate when the overlapping relationship of a particular organ at risk with respect to a target volume changes with respect to the treatment field. For example, in any given field, some part of a particular organ at risk may overlap with the target volume (and hence be subject to a required target dose level), another portion of the organ at risk, while not overlapping with the target volume, may nevertheless be within the ambit of the active or passive beam-shaping aperture (and hence be subject either to modulated fluence or so-called leaf-transmission fluence), and another portion of the organ at risk may be external to the field (and hence be essentially protected from fluence). (Fluence, of course, represents radiative flux integrated over time and comprises a fundamental metric in dosimetry (i.e., the measurement and calculation of an absorbed dose of ionizing radiation in matter and tissue).)

Figure 3:
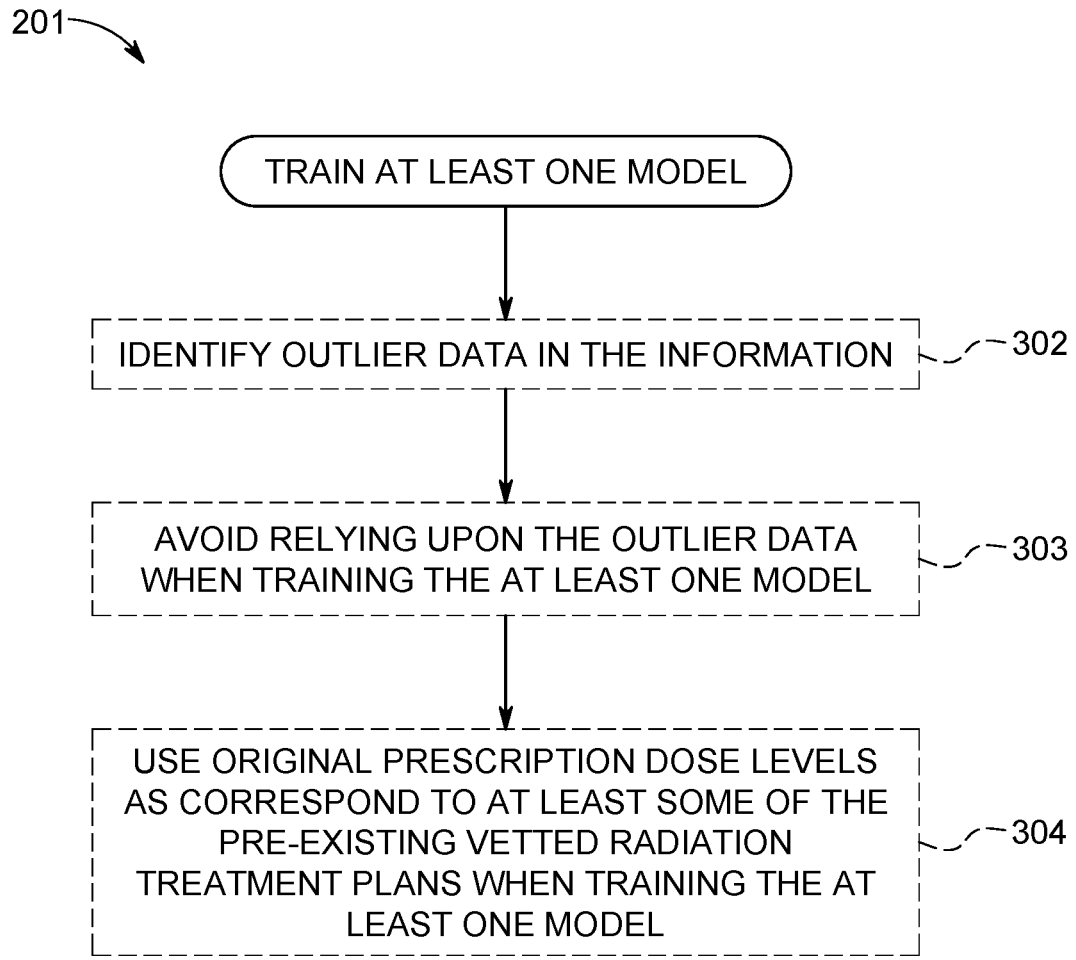
FIG. 3 comprises a flow diagram as configured in accordance with various embodiments of these teachings.

The use of models in general and of DVH estimation models in particular, and the training of models, constitutes a generally well-understood area of prior art endeavor. That said, and referring momentarily to FIG. 3, the training of the aforementioned DVH estimation model can benefit from one or more optional approaches in these regards.

As a first example in these regards, at blocks 302 and 303 this activity can include identifying outlier data in the information and then avoiding relying upon that outlier data when training the at least one model. When training a new DVH estimation model based on existing clinical data, it can be useful to create the training set from a coherent set of treatment plans. That said, such training will rely on complex metrics calculated from the treatment plans. Examples include organ overlap, DVH curve points, and in-field metrics, to note but a few. Identifying potential outliers by simply reviewing and comparing treatment plan parameters may be difficult in numerous real world settings.

These teachings contemplate visualizing various parameters used by a DVH estimation training algorithm that will allow a user to distinguish outliers in the training set. Parameters and visualizations can include, for example, DVH graphs, illustrating the data sets used by a regression analysis including regression lines, and a particular DVH estimated using the model against every patient geometry in the training set.

These teachings will also accommodate using a single numerical index for every training set plan comprised of various independent parameters calculated for that plan using the training algorithm of choice. Using a single outlier index can further aid the user to easily view the training set and distinguish outliers.

Figure 4:
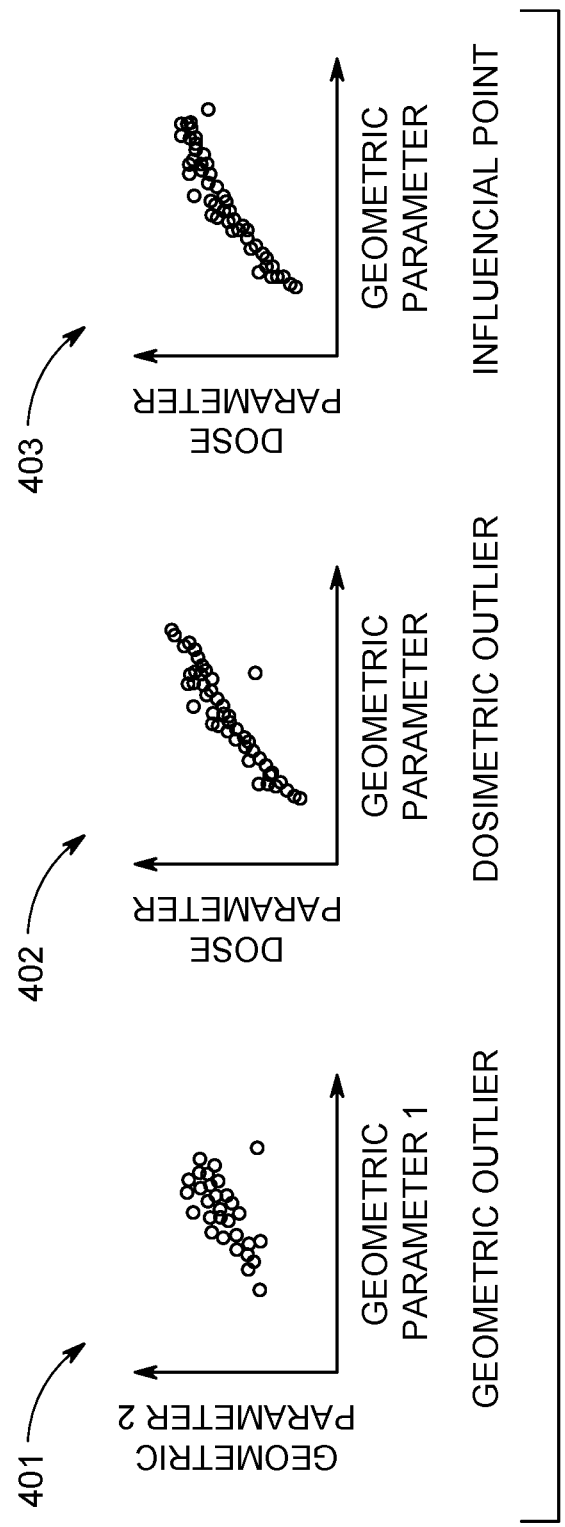
FIG. 4 comprises graphs as configured in accordance with various embodiments of these teachings.

FIG. 4 presents some illustrative examples in these regards. In particular, data may constitute an outlier by virtue of being a geometric outlier 401, a dosimetric outlier 402, or an influence point outlier 403.

As another example, and as illustrated at block 304, the control circuit 101 can be configured to use original prescription dose levels that correspond to at least some of the pre-existing vetted radiation treatment plans when training the model. For example, the control circuit 101 may use the original prescription dose levels when normalizing dose volume histograms.

Normalization, of course, typically affects the general scaling of corresponding estimates. If the normalization assumption at the time of estimation differs, for example, from what was used at the time of training the DVH estimation model, the estimates may be scaled sub-optimally.

Accordingly, the present teachings will accommodate obtaining the dose level of target structures in a particular training case from a corresponding dose matrix. That said, it will not typically be clear from a dose distribution alone which normalization has been used in a given instance. Accordingly, these teachings will accommodate the user providing, in addition to the dose matrix, a nominal dose level for the plan. The used normalization can then be deduced by comparing the target DVH and the user given dose level. The normalization information can also be used for other dose level deductions during the process of forming individual plans.

More specifically, these teachings will accommodate providing the user the opportunity to describe the intended dose level for each training set plan. This can comprise, for example, using the user-given dose level together with the dose distribution in target structures to define the user plan normalization during DVH estimation configuration. As another example, this can comprise using the determined plan normalization to scale other dose levels during DVH estimation configuration. And as yet another example, this can comprise using the determined plan normalization to back scale the user-given dose level during DVH estimation.

Referring again to FIG. 2, at optional block 203 the control circuit 101 can assess how well a particular patient fits the information 202 used to train the aforementioned model. As one specific example in these regards, the control circuit 101 conducts this assessment as a function of geometric limits 204 that corresponds to the information used to train the model. This approach can be particularly useful when the DVH estimation model contains information about the geometric limits (i.e., statistics of the independent model parameters) of the training set used for the model training.

Such an assessment can be useful because regression models, like most other models, are often valid only in a region spanned by the training set. For example, if all organ volumes of a certain organ at risk in a particular model are less than 5 deciliters, it will be difficult for such a model to work well in an application setting where the organ volume is 7 deciliters.

Accordingly, and specifically, these teachings will support providing, during estimation of a DVH, information regarding how well a current plan fits the training set used to train the DVH estimation model. As noted, this information can be statistics regarding independent geometric parameters of the training set plans. That said, in lieu of the foregoing or in combination therewith this information can be statistics of the dependent dose parameters of training set plans as compared to estimated dose parameters.

This information can then be used during the creation of estimates as described herein to check how well the current case is fitting to the training set.

When the control circuit 101 determines that the particular patient does not fit the information used to train the model within at least a predetermined range of suitability (determined, for example, at decision block 207), the control circuit 101 can present a user warning 208 via, for example, the aforementioned user interface 103.

At optional decision block 205 this process 200 can provide for determining a validation status of the aforementioned trained model. For example, the control circuit 101 can assess whether the model has been reviewed and validated by an authorized user or group of users. When not true, these teachings will accommodate inhibiting availability of that model (at block 206) unless and until the model is validated per the validation process of the user.

This capability can be particularly useful when models are shared between different application settings (for example, at different treatment clinics). In this case, a particular model can be validated at a receiving clinic to ensure that the model appropriately matches a local patient population and/or local treatment practices/platforms.

By one approach, availability of an un-validated model can be inhibited by preventing publication of the model at issue (where "publication" can refer to identifying information for the model being made available, internally or externally, to the relevant enterprise).

At block 209 the control circuit 101 uses the aforementioned trained model to develop estimates for a radiation treatment plan for a particular patient. There are various ways by which this can be accomplished. By one approach, for example, the DVH estimation model evaluates principal components of the area to be exposed for geometry-based expected dose volume histograms to thereby develop corresponding geometric parameters. Regression model coefficients can then be utilized to estimate corresponding DVH parameters using a regression model. The resultant DVH parameters can then be utilized to provide resultant DVH estimates for the particular patient.

Figure 5:
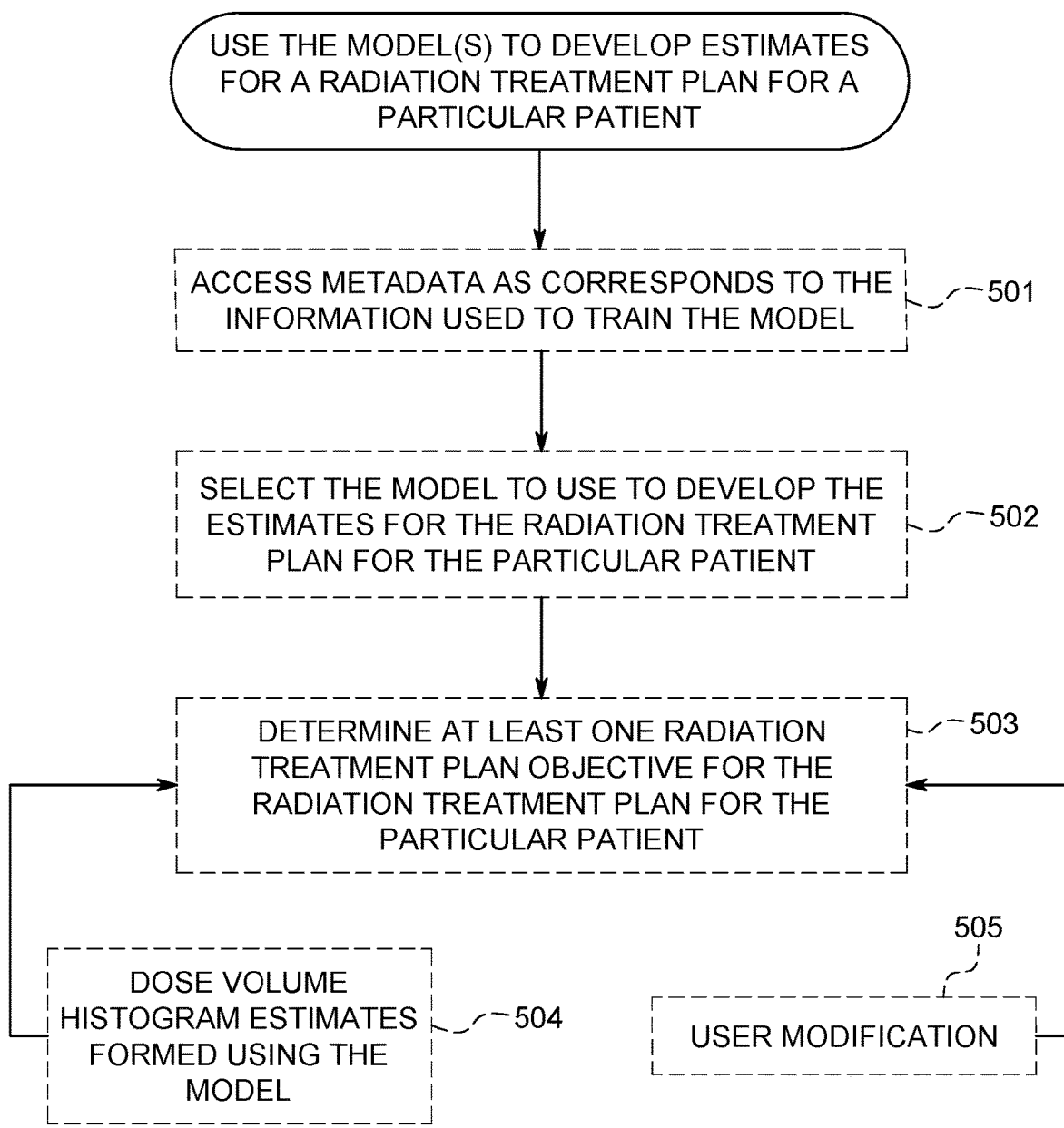
FIG. 5 comprises a flow diagram as configured in accordance with various embodiments of these teachings.

These teachings are highly flexible in these regards and will accommodate various additional approaches. FIG. 5 provides some illustrative examples in these regards.

At optional block 501, this activity can comprise accessing metadata as corresponds to the information used to train the model to help ensure selection of a suitable DVH estimation model for a particular patient. Useful examples of metadata include a model identifier, a short description of the model, a long description of the model (for example, in the form of an electronic document such as a datasheet that may include both text and non-textual graphics), and structured metadata associated with the model describing such things as biological structures, associated structure codes, and identification of the treatment site (such as the pelvis, thorax, and so forth).

At optional block 502, then, the control circuit can use that metadata to select a particular model to use when developing the estimates for the radiation treatment plan for the particular patient. For example, selection of a particular model can be based on structure definitions that are compared and automatically matched between the patient case and the DVH estimation model. So configured, selection of a particular model can be based on free-form textual information that contains clinically relevant description of the model's intended use.

By one approach, these teachings will also accommodate using such information to permit the control circuit to automatically propose a most suitable model for a particular patient as selected from amongst a plurality of available, validated models.

At optional block 503, this activity can comprise determining at least one radiation treatment plan objective for use when developing an optimized radiation treatment plan for the aforementioned particular patient. By one approach, the control circuit 101 determines this radiation treatment plan objective, at least in part, by forming the objective based upon dose volume histogram estimates 504 that were formed using the aforementioned model.

Clinical evaluation of radiation treatment plan quality often treats certain regions of a DVH as being more important than other areas. Specific priorities for different regions can depend on which organ at risk is being considered, the treatment modality, and other factors of choice. These teachings will also accommodate, if desired, providing a user opportunity (for example, via the aforementioned user interface 103) to modify the aforementioned radiation treatment plan objective and using that user input when determining this radiation treatment plan objective or objectives. For example, the user can have the opportunity to instruct the DVH estimation process to emphasize certain regions during the objective generation process.

By way of illustration, the configuration of a DVH estimation model can be leveraged by a user to deduce various dynamic objectives (that is, objectives whose exact location is deduced at the same time as are the DVH estimates). A user configuring a DVH estimation model can use these different objectives to provide guidance as regards the clinically important features in the DVH information.

Examples of dynamic objective include, but are not limited to, a point objective with a user-defined dose level (absolute or relative with respect to a prescription) where volume of the objective is dynamic, a point objective with a user-defined volume, a mean objective without a specified dose value, and a gEUD objective without a specified dose value. In all of these cases the user can have control with respect to some features of the generated objective while other features are deduced based on estimates. (In the case of a line objective that follows an estimated range other than in regions where the target overlaps with an organ at risk, the line objective can follow the target dose level if desired.)

Generally speaking, these teachings will accommodate generating objectives partly based on user-provided information and partly based on DVH estimations. More specifically, these teachings will accommodate:

generating a point objective where a user defines a desired dose level while volume parameters and priority are defined based on DVH estimates;

generating a point objective where the user defines a desired volume level while a dose parameter and priority are defined based on DVH estimates;

generating a mean-dose objective where a dose parameter and priority is defined based on DVH estimates;

generating a gEUD objective where the user defines the alpha parameter while dose parameter and priority are defined based on DVH estimates; and generating any of the foregoing where the user also defines the corresponding priority.

These teachings will also accommodate, as another illustrative example in these regards, generating line objectives while automatically handling overlap-to-target regions and transforming the objective line so that the latter does not conflict significantly with target objectives.

At optional block 210 this process 200 can use the aforementioned estimates for a radiation treatment plan to develop, in turn, a candidate radiation treatment plan for the particular patient. The use of input information to develop a radiation treatment plan comprises a well-understood area of prior art endeavor and requires no further elaboration here.

And at optional block 211 this process 200 can serve to display the aforementioned candidate radiation treatment plan via, for example, the aforementioned user interface 103.

DVH estimates (or, more generally, dose estimates) reflect achievable dosing for a defined prescription (often comprising target dose delineation and target dose level). Often these estimates are compared to a plan that is intended to be delivered to evaluate the quality of the plan. Unfortunately, changes in these regards can occur. For example, the intended plan may be re-normalized to a different dose level. (For example, this can occur when a treatment is interrupted and a remaining portion of the treatment is then re-planned.) When the target dose levels do not match, the resultant estimation for an organ at risk can be unacceptably high.

By one approach, the aforementioned display of information can include a simultaneous presentation of an overall target dose level that corresponds to the candidate radiation treatment plan. (By one approach the estimation target dose level is always displayed in combination with the prescribed dose level.) These teachings will accommodate, for example, presenting the dose estimation as a DVH and/or as a dose matrix. So configured, this approach can help a user confirm the lack of any mismatch between the dose level used in the estimation and the prescribed dose level in the intended plan.

The radiation-treatment platform 104 can then receive and utilize an approved radiation treatment plan as developed per the foregoing. In particular, the radiation-treatment platform 104 can employ the specifics of the approved radiation treatment plan when administering a radiation treatment to a particular patient.

Those skilled in the art will recognize that a wide variety of modifications, alterations, and combinations can be made with respect to the above described embodiments without departing from the scope of the invention, and that such modifications, alterations, and combinations are to be viewed as being within the ambit of the inventive concept.

What is claimed is:

1. An apparatus comprising:
   a memory having stored therein information regarding a plurality of pre-existing vetted radiation treatment plans for a variety of patients;
   a control circuit operably coupled to the memory and configured to:
      identify outlier data in the information;
      avoid relying upon at least some of the outlier data while training at least one model;
      develop estimates for a radiation treatment plan for a particular patient as a function, at least in part, of the at least one model.

2. The apparatus of claim 1 wherein the information regarding the plurality of pre-existing vetted radiation treatment plans for a variety of patients constitutes an abridged version of each of the pre-existing vetted radiation treatment plans such that the information is anonymous and not intrinsically correlated to any of the patients.

3. The apparatus of claim 1 wherein at least some of the plurality of pre-existing vetted radiation treatment plans have original formats that are different from one another and wherein the information regarding the plurality of pre-existing vetted radiation treatment plans presents contents of the pre-existing vetted radiation treatment plans in a single consistent format.

4. The apparatus of claim 1 wherein the control circuit is configured to identify the outlier data in the information, at least in part, as a function of dose volume histogram estimation training algorithm parameters.

5. The apparatus of claim 1 wherein the control circuit is configured to identify the outlier data in the information, at least in part, as a function of dose volume histogram graphs.

6. The apparatus of claim 1 wherein the control circuit is configured to identify the outlier data in the information, at least in part, as a function of regression lines corresponding to regression analysis data sets.

7. The apparatus of claim 1 wherein the control circuit is configured to identify the outlier data in the information, at least in part, as a function of a numerical index for each of the pre-existing vetted radiation treatment plans.

8. The apparatus of claim 7 wherein the control circuit is configured to calculate each of the numerical indexes as a function of a plurality of independent parameters calculated for each of the pre-existing vetted radiation treatment plans.

9. The apparatus of claim 1 wherein the control circuit is configured to identify the outlier data in the information, at least in part, as a function of identifying at least one of:
   a geometric outlier;
   a dosimetric outlier; and
   an influence point outlier.

10. A method comprising:
   providing a memory having stored therein information regarding a plurality of pre-existing vetted radiation treatment plans for a variety of patients;
   by a control circuit operably coupled to the memory:
   identifying outlier data in the information;
   avoiding relying upon at least some of the outlier data while training at least one model;
   developing estimates for a radiation treatment plan for a particular patient as a function, at least in part, of the at least one model.

11. The method of claim 10 wherein the information regarding the plurality of pre-existing vetted radiation treatment plans for a variety of patients constitutes an abridged version of each of the pre-existing vetted radiation treatment plans such that the information is anonymous and not intrinsically correlated to any of the patients.

12. The method of claim 10 wherein at least some of the plurality of pre-existing vetted radiation treatment plans have original formats that are different from one another and wherein the information regarding the plurality of pre-existing vetted radiation treatment plans presents contents of the pre-existing vetted radiation treatment plans in a single consistent format.

13. The method of claim 10 wherein identifying the outlier data in the information comprises identifying the outlier data in the information, at least in part, as a function of dose volume histogram estimation training algorithm parameters.

14. The method of claim 10 wherein identifying the outlier data in the information comprises identifying the outlier data in the information, at least in part, as a function of dose volume histogram graphs.

15. The method of claim 10 wherein identifying the outlier data in the information comprises identifying the outlier data in the information, at least in part, as a function of regression lines corresponding to regression analysis data sets.

16. The method of claim 10 wherein identifying the outlier data in the information comprises identifying the outlier data in the information, at least in part, as a function of a numerical index for each of the pre-existing vetted radiation treatment plans.

17. The method of claim 16 further comprising calculating each of the numerical indexes as a function of a plurality of independent parameters calculated for each of the pre-existing vetted radiation treatment plans.

18. The method of claim 10 wherein identifying the outlier data in the information comprises identifying the outlier data in the information, at least in part, as a function of identifying at least one of:
   a geometric outlier;
   a dosimetric outlier; and
   an influence point outlier.

* * * * *